US 6,491,631 B2

(12) United States Patent
Chiao et al.

(10) Patent No.: US 6,491,631 B2
(45) Date of Patent: *__Dec. 10, 2002__

(54) HARMONIC GOLAY-CODED EXCITATION WITH DIFFERENTIAL PULSING FOR DIAGNOSTIC ULTRASOUND IMAGING

(75) Inventors: Richard Yung Chiao, Menomonee Falls, WI (US); Theodore Lauer Rhyne, Whitefish Bay, WI (US)

(73) Assignee: General Electric Company, Niskayuna, NY (US)

( * ) Notice: Subject to any disclaimer, the term of this patent is extended or adjusted under 35 U.S.C. 154(b) by 57 days.

This patent is subject to a terminal disclaimer.

(21) Appl. No.: 09/757,762

(22) Filed: Jan. 11, 2001

(65) Prior Publication Data

US 2002/0091318 A1 Jul. 11, 2002

(51) Int. Cl.$^7$ .................................................. A61B 8/00

(52) U.S. Cl. ....................................... 600/443; 600/458

(58) Field of Search ................................ 600/437, 440, 600/441, 443, 447, 458, 472; 367/7, 138; 73/602

(56) References Cited

U.S. PATENT DOCUMENTS

| | | | |
|---|---|---|---|
| 5,632,277 | A | 5/1997 | Chapman et al. |
| 5,706,819 | A | 1/1998 | Hwang et al. |
| 5,951,478 | A | 9/1999 | Hwang et al. |
| 5,984,869 | A | 11/1999 | Chiao et al. |
| 6,050,947 | A | 4/2000 | Rhyne et al. |
| 6,146,328 | A | 11/2000 | Chiao et al. |
| 2001/0044278 | A1 * | 11/2001 | Chiao et al. ............... 455/67.1 |

OTHER PUBLICATIONS

"Coded Excitation for Harmonics Imaging," Y. Takeuchi, IEEE Proceedings of the International Ultrasonics Symposium, vol. 2, 1996, pp. 1433–1436.

"A New Imaging Technique Based on the Nonlinear Properties of Tissues," MA Averkiou, DN Roundhill; JE Powers, IEEE Proceedings of the Ultrasonics Symposium, vol. 2, 1997, pp. 1561–1566.

"Characteristics of Contrast Agents and 2D Imaging," IEEE Proceedings of the International Ultrasonics Symposium, vol. 2, 1996, pp. 1449–1458.

"Enhanced Tissue–Generated Harmonic Imaging By Coded Excitation," RY Chiao, Y. Takeuchi, Al Hall, KE Thomenius, Ser. No. 09/494,465 (GE docket No. RD–26,177), filed Jan. 31, 2000.

* cited by examiner

Primary Examiner—Marvin M. Lateef
Assistant Examiner—Ali M. Imam
(74) Attorney, Agent, or Firm—Jill M. Breedlove; Christian G. Cabou

(57) ABSTRACT

Harmonic imaging using harmonic Golay-coded excitation that encodes the fundamental and second harmonic signals utilizes the transmit sequences encoded using QPSK implemented as quarter-cycle circular rotations or shifts of the base pulse. This is implemented by time shifting the chips of the transmit sequence encoded with a "j" or "–j" code symbol by ¼ fractional cycle at center frequency relative to the chips encoded with a "1" or "–1" code symbol. A different QPSK transmit code is used for each of four transmits A, B, C and D. The transmit codes are selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair. The coding and decoding technique achieves fundamental suppression and second harmonic compression for a given Golay code pair X and Y.

24 Claims, 5 Drawing Sheets

HARMONIC GOLAY-CODED EXCITATION WITH DIFFERENTIAL PULSING FOR DIAGNOSTIC ULTRASOUND IMAGING

BACKGROUND OF THE INVENTION

This invention relates to ultrasound imaging systems and more particularly, to methods for harmonic ultrasound imaging using coded excitation.

BACKGROUND OF THE INVENTION

Conventional ultrasound imaging systems comprise an array of ultrasonic transducer elements which transmit an ultrasound beam and then receive the reflected beam from the object being studied. Such operation comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is dynamically focused at a succession of ranges along the scan line as the reflected ultrasonic waves are received.

For ultrasound imaging, the array typically has a multiplicity of transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred vector direction and is focused at a selected point along the beam. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. For a steered array, by changing the time delays and amplitudes of the applied voltages, the beam with its focal point can be moved in a plane to scan the object. For a linear array, a focused beam directed normal to the array is scanned across the object by translating the aperture across the array from one firing to the next.

The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element.

An ultrasound image is composed of multiple image scan lines. A single scan line (or small localized group of scan lines) is acquired by transmitting focused ultrasound energy at a point in the region of interest, and then receiving the reflected energy over time. The focused transmit energy is referred to as a transmit beam. During the time after transmit, one or more receive beamformers coherently sum the energy received by each channel, with dynamically changing phase rotation or time delays, to produce peak sensitivity along the desired scan lines at ranges proportional to the elapsed time. The resulting focused sensitivity pattern is referred to as a receive beam. Resolution of a scan line is a result of the directivity of the associated transmit and receive beam pair.

The output signal of the beamformer channels are coherently summed to form a respective pixel intensity value for each sample volume in the object region or volume of interest. These pixel intensity values are log-compressed, scan-converted and then displayed as an image of the anatomy being scanned.

Conventional ultrasound transducers transmit a broadband signal centered at a fundamental frequency $f_0$, which is applied separately by a respective pulser to each transducer element making up the transmit aperture. The pulsers are activated with time delays that produce the desired focusing of the transmit beam at a particular transmit focal position. As the transmit beam propagates through tissue, echoes are created when the ultrasound wave is scattered or reflected off of the boundaries between regions of different density. The transducer array is used to convert these ultrasound echoes into electrical signals, which are processed to produce an image of the tissue. These ultrasound images are formed from a combination of fundamental (linear) and harmonic (nonlinear) signal components, the latter of which are generated in nonlinear media such as tissue or a blood stream containing contrast agents. With scattering of linear signals, the received signal is a time-shifted, amplitude-scaled version of the transmitted signal. This is not true for acoustic media which scatter nonlinear ultrasound waves.

The echoes from a high-level signal transmission contain both linear and nonlinear signal components. In certain instances ultrasound images may be improved by suppressing the fundamental signal and emphasizing the harmonic (nonlinear) signal components. If the transmitted center frequency is at $f_0$, then tissue/contrast nonlinearities will generate harmonics at $kf_0$ and subharmonics at $f_0/k$, where k is an integer greater than or equal to 2. (The term "(sub)harmonic" refers to harmonic and/or subharmonic signal components.) Imaging of harmonic signals has been performed by transmitting a narrow-band signal at second harmonic frequency $f_0$ and receiving at a band centered at frequency $2f_0$ followed by receive signal processing.

Tissue-generated harmonic imaging is capable of greatly improving B-mode image quality in difficult-to-image patients. One fundamental problem faced by tissue-generated harmonic imaging is low harmonic-to-noise ratio (HNR) since the harmonic signals are at least an order of magnitude lower in amplitude than the fundamental signal. A secondary problem is insufficient isolation of the harmonic signal from the fundamental as measured by a low harmonic-to-fundamental ratio (HFR).

Coded Excitation is the transmission of long encoded pulse sequences and decoding of the received signals in order to improve image SNR and/or resolution. The energy contained in a long transmit pulse sequence is compressed into a short time interval on receive by virtue of the code. Coded excitation is a well-known technique in medical ultrasound imaging. For example, the use of Golay codes is disclosed in U.S. Pat. No. 5,984,869 issued on Nov. 16, 1999 and assigned to the instant assignee.

Likewise the techniques of tissue harmonic imaging and harmonic imaging using contrast agents are known. Harmonic imaging images the nonlinear signal components produced inside the body that are used to both reduce clutter when imaging tissue and to enhance contrast agent signal when imaging blood flow. The technique of tissue harmonic imaging is presented in Averkiou et al., "A New Imaging Technique Based on the Nonlinear Properties of Tissues," Proc. 1997 IEEE Ultrasonics Symp., pp. 1561–1566 (1998), while harmonic imaging using contrast agents is presented in de Jong et al., "Characteristics of Contrast Agents and 2D Imaging," Proc. 1996 IEEE Int'l Ultrasonics Symp., pp. 1449–1458 (1997). Tissue harmonics can greatly improve B-mode image quality in difficult-to-image patients, while contrast harmonics can greatly improve vascular studies.

Harmonic imaging that uses two transmits with 180-degree phase shifts has been disclosed. Pulse inversion between the two transmits suppresses the fundamental signal and leaves the harmonic signal to form the image. Harmonic coded excitation that uses pulse sequences with 0 and 90-degree phase symbols (e.g., "1" and "j", where $j^2=-1$) has been disclosed by Takeuchi in "Coded Excitation for Harmonic Imaging," Proc. 1996 IEEE Int'l Ultrasonics Symp., pp. 1433–1436 (1997) and by Chiao et al. in U.S. patent application Ser. No. 09/494,465 filed on Jan. 31, 2000. However, a method to suppress the fundamental signal on reception was not specified in those disclosures. Harmonic coded excitation using Quadrature Phase Shift Keying (QPSK) (i.e., symbols 1, −1, j and −j) with suppression of the fundamental signal on reception was disclosed in U.S. Pat. No. 6,050,947 issued on Apr. 18, 2000 and assigned to the instant assignee.

There is need for a harmonic imaging technique which does not use transmits that are 180 degrees apart and in which complete pulse compression is not prevented due to spectral mismatch between "plus" and "minus" harmonic pulses (particularly for broadband pulses).

SUMMARY OF THE INVENTION

Harmonic imaging using harmonic Golay-coded excitation encodes the fundamental and second harmonic signals, and subsequently performs decoding on reception to suppress the fundamental signal and to compress the second harmonic signal. Using this technique, the SNR and/or resolution of the second harmonic image can be improved. In accordance with the preferred embodiments of the invention, four encoded sequences are transmitted to generate two fundamental and two second harmonic Golay-encoded pulse sequences on reception. Upon decoding of these received sequences, the fundamental signal is suppressed and the second harmonic signal is compressed.

More specifically, the amplitude of the transmitted pulse sequences is set sufficiently high to generate harmonic signals from the nonlinearity of the tissue. For each transmit focal zone, four separately encoded sequences are transmitted, received, filtered, and combined to form the decoded (compressed) second harmonic signal with fundamental component suppressed. This process is then repeated for subsequent focal zones to form an entire image frame.

In accordance with the preferred embodiments, the transmit sequences are encoded using QPSK implemented as quarter-cycle circular rotations or shifts of the base pulse. This is implemented by time shifting the chips of the transmit sequence encoded with a "j" or "−j" code symbol by ¼ fractional cycle at center frequency relative to the chips encoded with a "1" or "−1" code symbol. (The QPSK transmit code symbols are "1", "−1", "j" and "−j".) For the second harmonic signal, the phases of the chips of the encoded transmit sequence are 90° apart, which is implemented by circularly shifting the one chip by a quarter cycle in a transmit sequence memory. (The term "circularly shifting" as used herein means that the time samples which are dropped at the front end of a shifted chip are added at the back end of the shifted chip.)

A different QPSK transmit code is used for each of four transmits A, B, C and D. The transmit codes are selected such that (A–B) and (C–D) are encoded by $\underline{Y}$ and −$\underline{X}$, respectively, while ($A^2-B^2$) and ($C^2-D^2$) are encoded by X and Y, respectively, where X and Y form a Golay code pair. X is a sequence such that X=x(n), n=0, 1, 2, ..., (N−1), and $\underline{X}$ denotes the reversal of X given by $\underline{X}$=x(N−1−n) for n=0, 1, 2, ..., (N−1). The same is true for Y and $\underline{Y}$. A Golay code pair X and Y satisfies the complementarity property X*$\underline{X}$+Y*$\underline{Y}$=δ(n), where the "*" symbol denotes convolution and δ(n) is a Kronecker delta function.

The coding and decoding technique disclosed herein achieves fundamental suppression and second harmonic compression for a given Golay code pair X and Y. The received signal from the second transmit is subtracted from that of the first transmit, and the received signal from the fourth transmit is subtracted from that of the third transmit to form the Golay-encoded fundamental and Golay-encoded second harmonic signals. Formation of the encoded harmonic signal from the difference of two received signals is necessary to equalize the spectra of the second harmonic signals representing the "plus" and "minus" code symbols, since the second harmonic signals generated from different QPSK transmit pulses may not be exactly inverted in phase (e.g., the second harmonic response of the "j" pulse may not be equal to the negative of the second harmonic response of the "1" pulse). The Golay-encoded harmonic signals are then compressed by matched filtering and summing the filter outputs, thereby canceling the fundamental signal to leave the second harmonic signal for image formation.

DETAILED DESCRIPTION OF THE PREFERRED EMBODIMENTS

Figure 1:
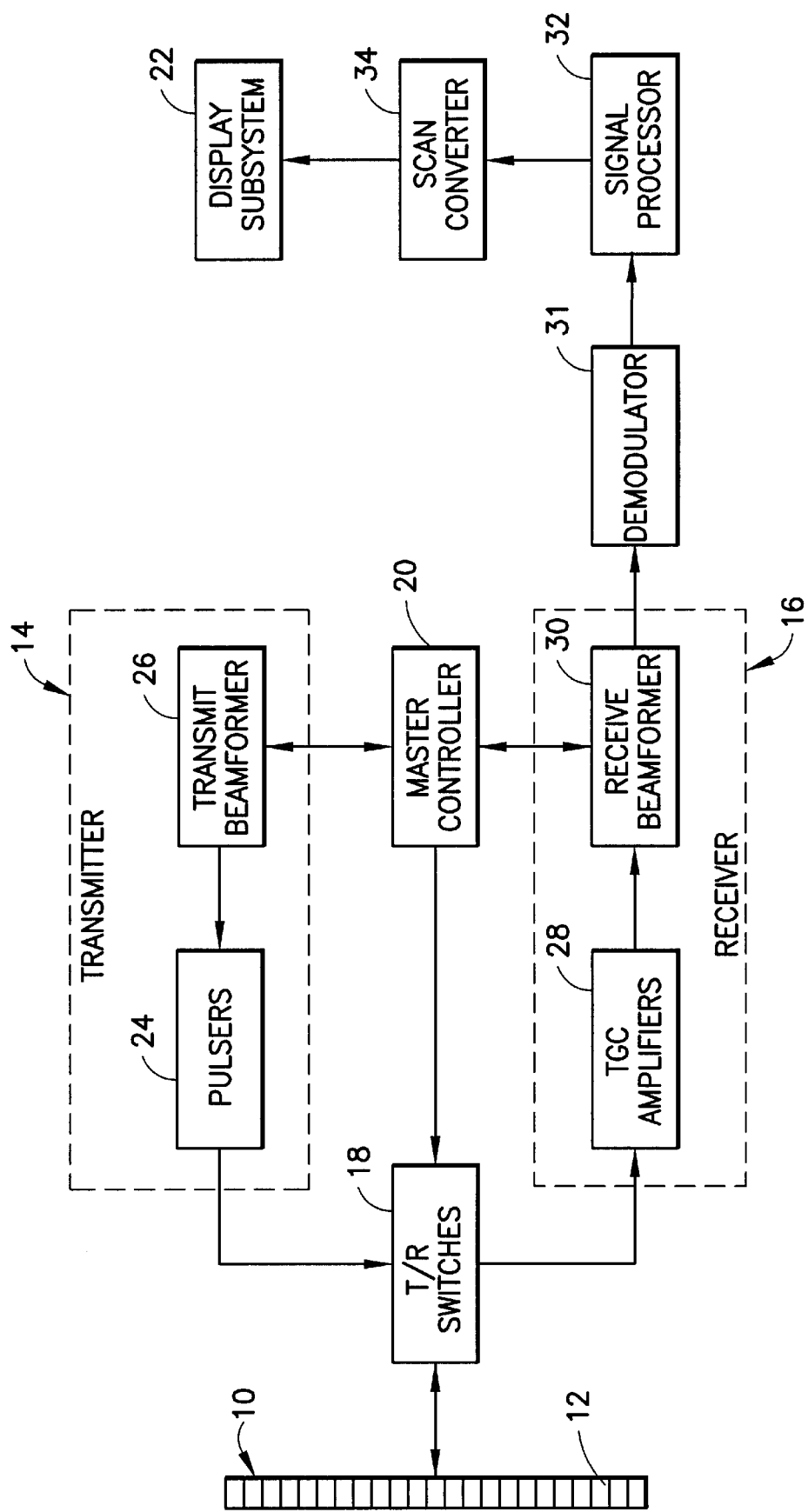
FIG. 1 is a block diagram of a conventional ultrasound imaging system.

An ultrasonic imaging system in which the present invention can be incorporated is depicted in FIG. 1. The system comprises a transducer array 10 made up of a plurality of separately driven transducer elements 12, each of which produces a burst of ultrasonic energy when energized by a pulsed waveform produced by a transmitter 14. The ultrasonic energy reflected back to transducer array 10 from the object under study is converted to an electrical signal by each receiving transducer element 12 and applied separately to a receiver 16 through a set of transmit/receive (T/R) switches 18. The T/R switches 18 are typically diodes which protect the receive electronics from the high voltages generated by the transmit electronics. The transmit signal causes the diodes to shut off or limit the signal to the receiver. Transmitter 14 and receiver 16 are operated under control of a master controller (e.g., a host computer) 20 responsive to commands supplied by a human operator via an operator interface (not shown). A complete scan is performed by acquiring a series of echoes in which transmitter 14 is gated ON momentarily to energize each transducer element 12, and the subsequent echo signals produced by each transducer element 12 are applied to receiver 16. A channel may begin reception while another channel is still transmitting. Receiver 16 combines the separate echo signals from each transducer element to produce a single echo signal which is used to produce a line in an image on a display monitor 22.

Under the direction of master controller 20, transmitter 14 drives transducer array 10 such that the ultrasonic energy is transmitted as a directed focused beam. To accomplish this, respective time delays are imparted to a multiplicity of pulsers 24 by a transmit beamformer 26. Master controller 20 determines the conditions under which the acoustic pulses will be transmitted. With this information, transmit beamformer 26 determines the timing and amplitudes of each of the transmit pulses to be generated by pulsers 24. The amplitudes of each transmit pulse are generated by an apodization generation circuit (not shown). Pulsers 24 in turn send the transmit pulses to each of elements 12 of the transducer array 10 via the T/R switches 18, which protect time-gain control (TGC) amplifiers 28 from the high voltages which may exist at the transducer array. By appropriately adjusting the transmit focus time delays and the apodization weightings in conventional manner, an ultrasonic beam can be directed and focused to form a transmit beam.

The echo signals produced by each burst of ultrasonic energy reflect from objects located at successive ranges along each transmit beam. The echo signals are sensed separately by each transducer element 12 and a sample of the magnitude of the echo signal at a particular point in time represents the amount of reflection occurring at a specific range. Due to differences in the propagation paths between a reflecting point and each transducer element 12, the echo signals are not detected simultaneously and their amplitudes are not equal. Receiver 16 amplifies the separate echo signals via a respective TGC amplifier 28 in each receive channel. TGC is carried out by increasing or decreasing gain as a function of depth. The amount of amplification provided by the TGC amplifiers is controlled through a control line (not shown) that is driven by a TGC circuit (not shown), the latter being set by the host computer and hand operation of potentiometers. The analog echo signals are then sent to receive beamformer 30.

Under the direction of master controller 20, receive beamformer 30 tracks the direction of the transmitted beam, sampling the echo signals at a succession of ranges along each beam. Receive beamformer 30 imparts the proper time delays and receive apodization weightings to each amplified echo signal and sums them to provide an echo signal that accurately indicates the total ultrasonic energy reflected from a point located at a particular range along one ultrasonic beam. The receive focus time delays are computed in real-time using specialized hardware or are read from a lookup table. The receive channels also have circuitry for filtering the received pulses. The time-delayed receive signals are then summed.

In the system shown in FIG. 1, the beamformer output frequency is shifted to baseband by a demodulator 31. One way of achieving this is to multiply the input signal by a complex sinusoidal $e^{j2\pi f_d t}$, where $f_d$ is the frequency shift required to bring the signal spectrum to baseband. The demodulated signals are then supplied to a signal processor 32. Signal processor 32 converts the demodulated signals to display data. In the B-mode (gray-scale), the display data would be the envelope of the signal with some additional processing, such as edge enhancement and logarithmic compression.

In another conventional system, the RF signals are summed, equalized and envelope detected without intervening demodulation to baseband. To depict such system, it is only necessary to remove demodulator 31 from FIG. 1 and connect the output of the beamformer 30 to the input of signal processor 32. It should be appreciated that the invention can be employed in both RF and baseband systems.

In general, the display data are converted by scan converter 34 into X-Y format for video display. The scan-converted frames are passed to a video processor (not shown) incorporated in display subsystem 22. The video processor maps the video data for display and sends the mapped image frames to the display subsystem.

The images displayed by the video monitor (not shown) of display subsystem 22 are produced from an image frame of data in which each datum indicates the intensity or brightness of a respective pixel in the display. An image frame may, e.g., comprise a 400×500 data array in which each intensity datum is an 8-bit binary number that indicates pixel brightness. The brightness of each pixel on the display monitor is continuously refreshed by reading the value of its corresponding element in the data array in a well-known manner. Each pixel has an intensity value which is a function of the backscatter cross section of a respective sample volume in response to interrogating ultrasonic pulses.

Figure 2:
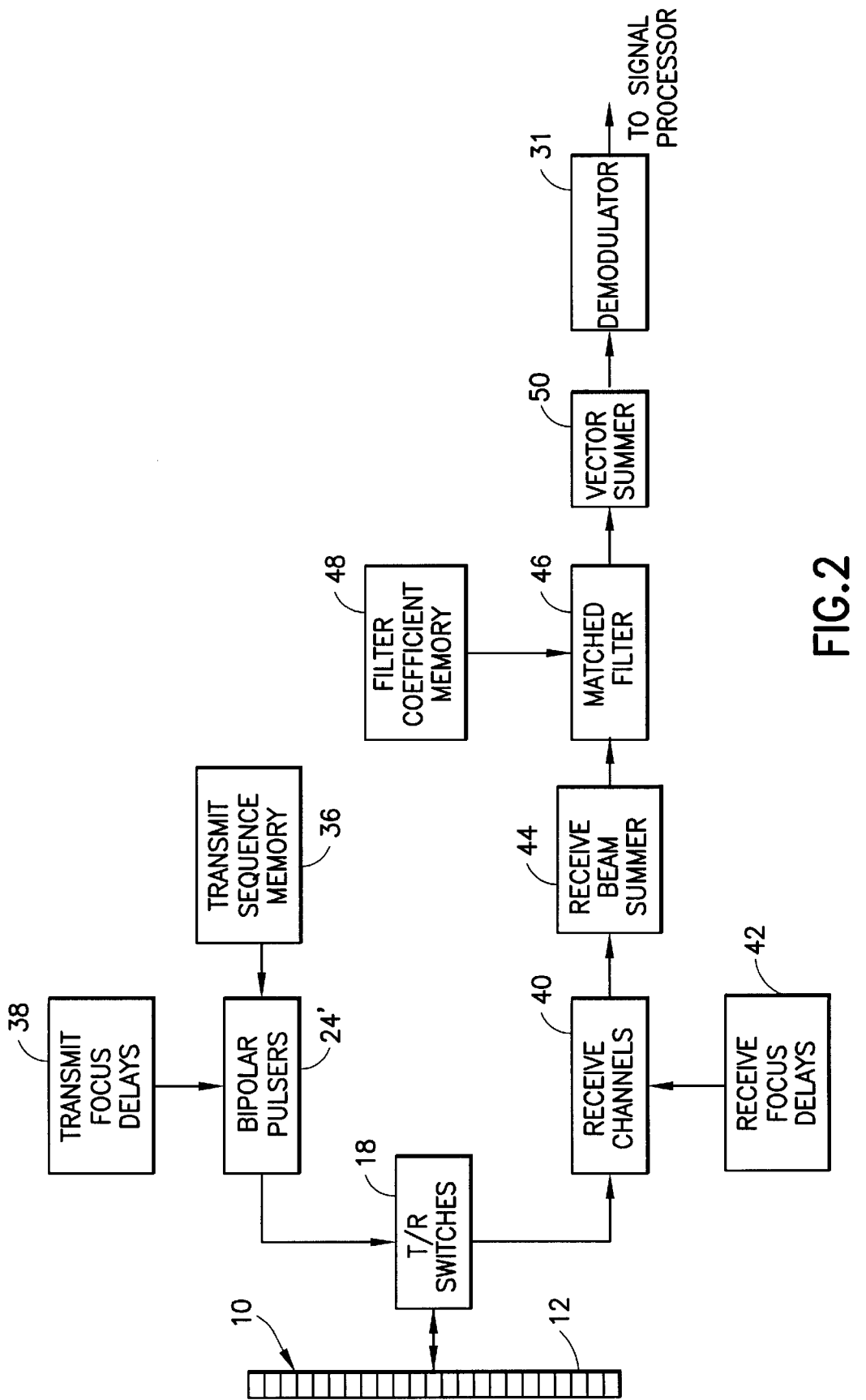
FIG. 2 is a block diagram showing of an ultrasound imaging system in accordance with one preferred embodiment of the invention.
Figure 3:
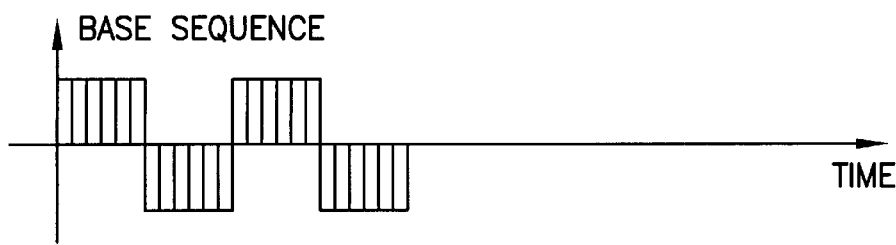
FIGS. 3–6 are pulse diagrams showing a base sequence (FIG. 3), an oversampled code sequence (FIG. 4), an encoded transmit sequence for fundamental imaging (FIG. 5), and an encoded transmit sequence for harmonic imaging (FIG. 6).
Figure 4:
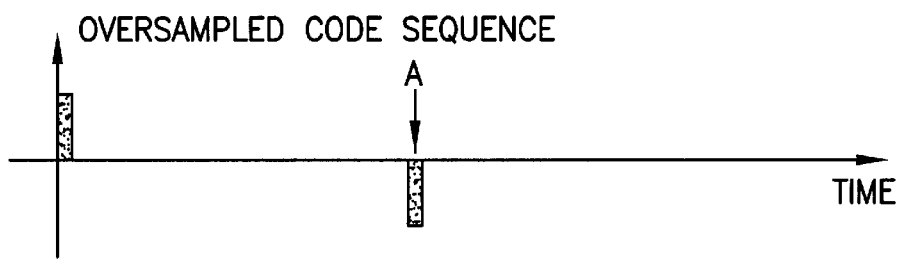

FIG. 2 shows a preferred embodiment of the invention employing coded excitation for the display of a harmonic image. In this system each transducer element in the transmit aperture is pulsed using an encoded transmit sequence, each pulse in the sequence being commonly referred to as a chip. The encoded transmit sequence is formed by convolving a base sequence (comprising a sequence of +1 and −1 elements) with an oversampled code sequence (comprising an n-digit code, each digit being either of two code symbols, +1 and −1). In particular, the base sequence is phase encoded, using an n-digit code sequence, to create an n-chip encoded transmit sequence. In the preferred embodiment, four different n-chip encoded transmit sequences are stored in a transmit sequence memory 36.

Figure 5:
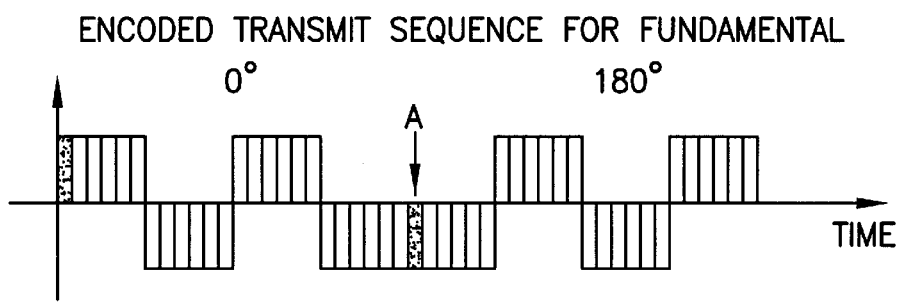
Figure 6:
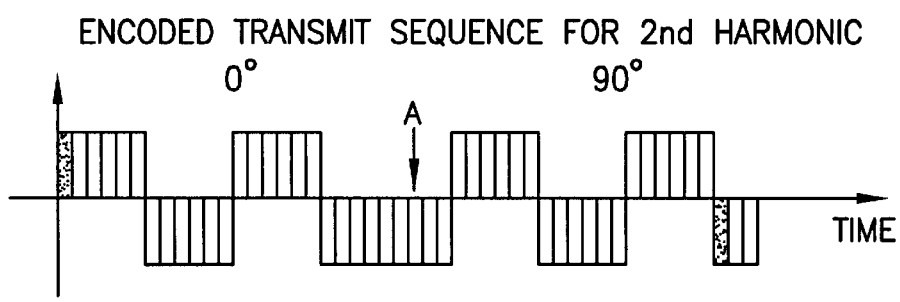

The generation of an exemplary encoded transmit sequence for use in harmonic imaging in accordance with a preferred embodiment of the invention is shown in FIGS. 3–6. FIG. 5 shows an encoded transmit sequence wherein the second chip is phase-shifted by 180° relative to the first chip. FIG. 6 shows an encoded transmit sequence wherein the second chip is phase-shifted by 90° relative to the first chip. In each instance the code sequence is not transmitted directly but rather by first oversampling (typically at 40 MHz or dt=0.025 μsec time samples) and then convolving the oversampled code sequence (shown in FIG. 4) with a base sequence (shown in FIG. 3) to form the encoded transmit sequences. The start of the chip encoded with the second code symbol of the code sequence is designated by the letter "A" in FIGS. 5 and 6. The encoded transmit sequence can be transmitted much more efficiently since its spectrum is better matched to the transducer passband with proper selection of the base sequence.

Conventional biphase codes, such as Barker and Golay codes, have two phase-inverted symbols such as +1 and −1. However, to encode the transmit waveform for acquiring the N-th harmonic signal using the code symbols of the code sequence shown in FIG. 4, the chip of the transmit waveform encoded with the second code symbol (i.e., −1) needs to be phase-shifted by 180°/M relative to the chip encoded with the first code symbol (i.e., +1). This is because if the transmitted signal has a phase term exp[jθ], then the received N-th harmonic signal has a phase term exp[jNθ]. In particular, to encode the transmit waveform for acquiring the second (N=2) harmonic signal, the respective chips corresponding to the two code symbols +1 and −1 must be 90° apart in order for the respective second harmonic receive signals to be 180° apart.

The phase shift in the encoded transmit sequence corresponding to the second code element is implemented by circularly shifting the corresponding chip in time by T=1/(2Nf$_0$) μsec, where N is the harmonic order and f$_0$ is the fundamental (i.e., transmit) center frequency in MHz. For example, for N=2 (second harmonic) and f$_0$=3.33 MHz, the time shift is T=0.075 μsec, which corresponds to T/dt=3 time samples. The chip in the encoded transmit sequence corresponding to a 90° phase shift is then circularly shifted in time by 3 time samples, the first of the 3 shifted time samples being shaded in FIG. 6. This is implemented by circularly shifting the second chip by a quarter cycle in the transmit sequence memory.

In the system of FIG. 2, each encoded transmit sequence read out of transmit sequence memory 36 controls activation of a multiplicity of bipolar pulsers 24' during a respective transmit firing. The encoded transmit sequence for a given focal position is transmitted with sufficient amplitude such that harmonic signals are generated from nonlinear propagation in tissue. Pulsers 24' drive the transducer elements 12 making up the transmit aperture such that the ultrasonic energy produced is focused in a beam for each transmit firing. To accomplish this, transmit focus time delays stored in a lookup table 38 are imparted to the respective pulsed waveforms produced by the pulsers. By appropriately adjusting the transmit focus time delays in a conventional manner, the ultrasonic beams can be focused at a multiplicity of transmit focal positions to effect a scan in an image plane. During each firing, bipolar pulsers 24' can be excited by an encoded transmit sequence provided from transmit sequence memory 36 or from specialized hardware.

For each transmit, the echo signals from transducer elements from transducer elements 12 are fed to respective receive channels 40 of the receive beamformer. Each receive channel has both a TGC amplifier and an analog-to-digital converter (not shown in FIG. 2). Under the direction of master controller 20 (FIG. 1), the receive beamformer tracks the direction of the transmitted beam. Receive beamformer memory 42 imparts the proper receive focus time delays to the received echo signals and sums the signals to obtain an echo signal that accurately represents the total ultrasonic energy reflected from a particular transmit focal position. The time-delayed receive signals are summed in receive beamsummer 44 for each transmit firing.

For four-transmit coded excitation, the beamsummed receive signals acquired following each transmit firing are supplied to a matched filter 46 that convolves each beamsummed receive signal with a respective receive code. Preferably, matched filter 46 comprises a finite impulse response (FIR) filter. Suitable filter coefficients are stored in memory 48 and are supplied to matched filter 46 at the appropriate times.

In accordance with a preferred embodiment of the invention, the summed receive signals from first through fourth successive firings are supplied to matched filter 46, which convolves the first summed receive signal with a first receive code for the first transmit firing, the second summed receive signal with a second receive code for the second transmit firing, and so forth. The match-filtered signals derived from the first through fourth transmit firings focused at the same transmit focal position are summed in a vector summer 50. Matched filter 46 and vector summer 50 together perform pulse compression of the harmonic signal and suppression of the fundamental signal.

The filtered and summed receive signal is demodulated by demodulator 31 and supplied to signal processor 32 (FIG. 1). In the B mode, signal processing includes envelope detection, edge enhancement and logarithmic compression. After signal processing and scan conversion, a scan line is displayed on the display monitor. This procedure is repeated so that a respective scan line is displayed for each transmit focal position (in the situation of one transmit focal position for each beam angle) or for each vector (in the situation of multiple transmit focal positions for each beam angle), thereby forming a harmonic image of the desired order.

For four-transmit coded excitation in accordance with a preferred embodiment of the invention, the transmit sequences are generated using QPSK implemented as quarter-cycle circular rotations or shifts of the base pulse. The QPSK transmit code symbols are "1", "−1", "j" and "−j". The QPSK is implemented by time-shifting the chips of the transmit sequence encoded with a "j" or "−j" code symbol by ¼ fractional cycle at center frequency relative to the chips encoded with a "1" or "−1" code symbol, as demonstrated in FIG. 6. For the code symbol "1", for example, the base pulse [1, 1, −1, −1], can be transmitted, implying that the phase-inverted base pulse [−1, −1, 1, 1] would correspond to the "−1" symbol. The right quarter-cycle rotation of the base pulse [−1, 1, 1, −1] can be further assigned to be the "j" symbol, which then implies that the "−j" symbol would be the left quarter-cycle rotation [1, −1, −1, 1].

In accordance with a preferred embodiments of the invention, a different QPSK transmit code is used for each of four transmits A, B, C and D. The transmit codes are selected such that (A−B) and (C−D) are encoded by $\underline{Y}$ and $-\underline{X}$, respectively, while ($A^2-B^2$) and ($C^2-D^2$) are encoded by X and Y, respectively, where X and Y form a Golay code pair, X is a sequence such that X=x(n), n=0, 1, 2, ..., (N−1), and $\underline{X}$ denotes the reversal of X given by $\underline{X}$=x(N−1−n) for n=0, 1, 2, ..., (N−1). The same is true for Y and $\underline{Y}$.

Figure 7:
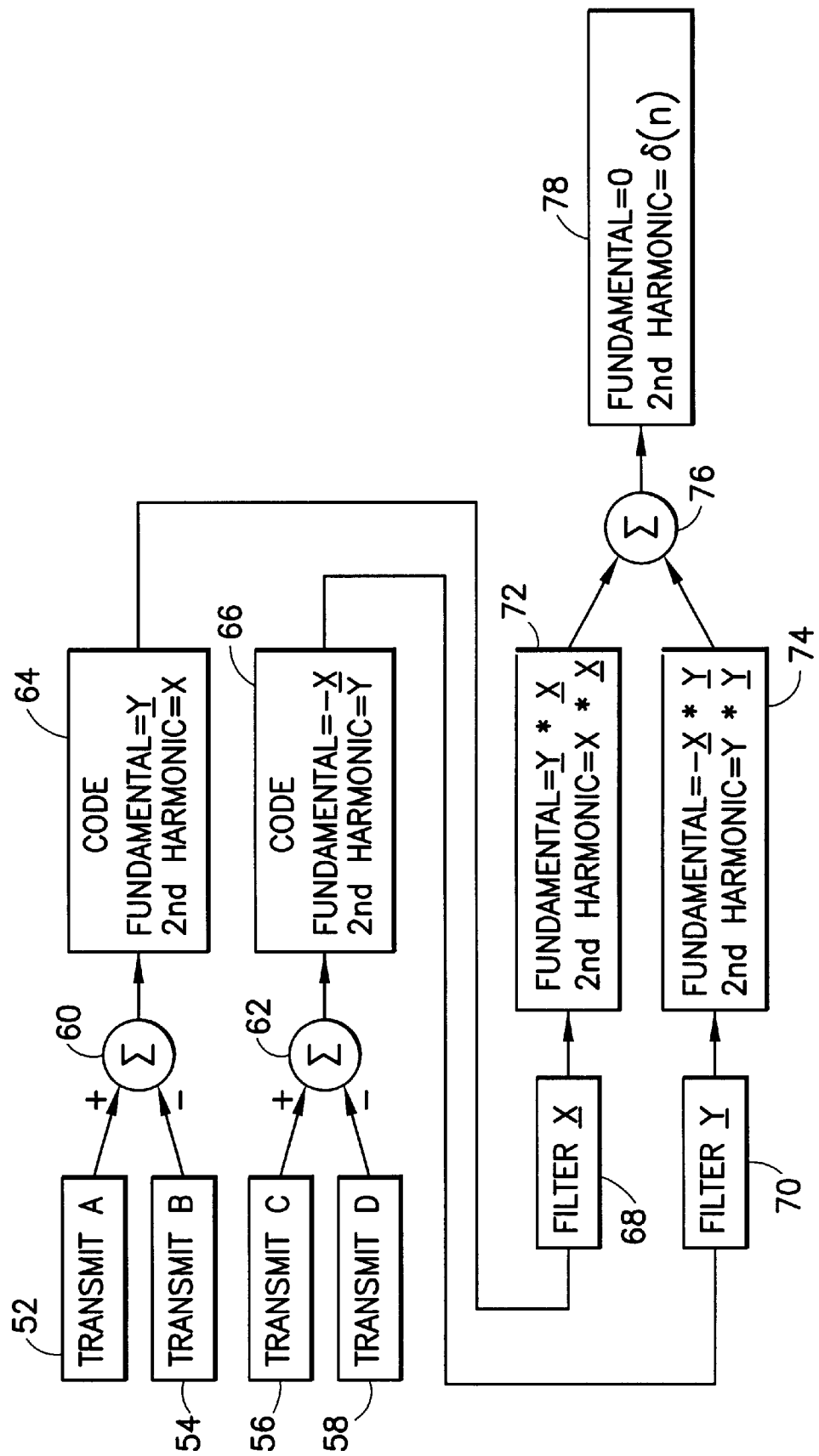
FIG. 7 is a block diagram illustrating a coding and decoding scheme for a Golay code pair (X, Y) in accordance with one preferred embodiment of the invention.

FIG. 7 shows the coding and decoding method for to achieving fundamental suppression and second harmonic compression for a given Golay code pair X and Y. The received signal 54 resulting from the second transmit B is subtracted from the received signal 52 resulting from the first transmit A in an adder/subtracter 60, and the received signal 58 resulting from the fourth transmit D is subtracted from the received signal 56 of the third transmit C in an adder/subtracter 62 to form the Golay-encoded fundamental 64 and Golay-encoded second harmonic 66 signals. Formation of the encoded harmonic signal from the difference of two received signals is necessary to equalize the spectra of the second harmonic signals representing the "plus" and "minus" code symbols, since the second harmonic signals generated from different QPSK transmit pulses may not be exactly inverted in phase (e.g., the second harmonic response of the "j" pulse may not be equal to the negative of the second harmonic response of the "1" pulse). The Golay-encoded harmonic signals are then compressed by matched filtering 68 and 70,) and summing the filter output signals 72 and 74 in a summer 76). With the particular selection of Golay code on the fundamental signal given above, this same filtering and summation cancels the fundamental signal to leave the second harmonic signal for image formation.

To implement the disclosed coding method, four QPSK transmit sequences A, B, C, and D are generated from a given Golay code pair X and Y as follows (where A→B denotes replacing every occurrence of "A" by "B" and the triple product is performed element-by-element):

$$A = X\underline{Y}X(-1 \to j) \quad (1)$$

$$B = X\underline{Y}X(\{1 \to j\}, \{-1 \to 1\}) \quad (2)$$

$$C = -\underline{X}YY(-1 \to j) \quad (3)$$

$$D = -\underline{X}YY(\{1 \to j\}, \{-1 \to 1\}) \quad (4)$$

Figure 8:
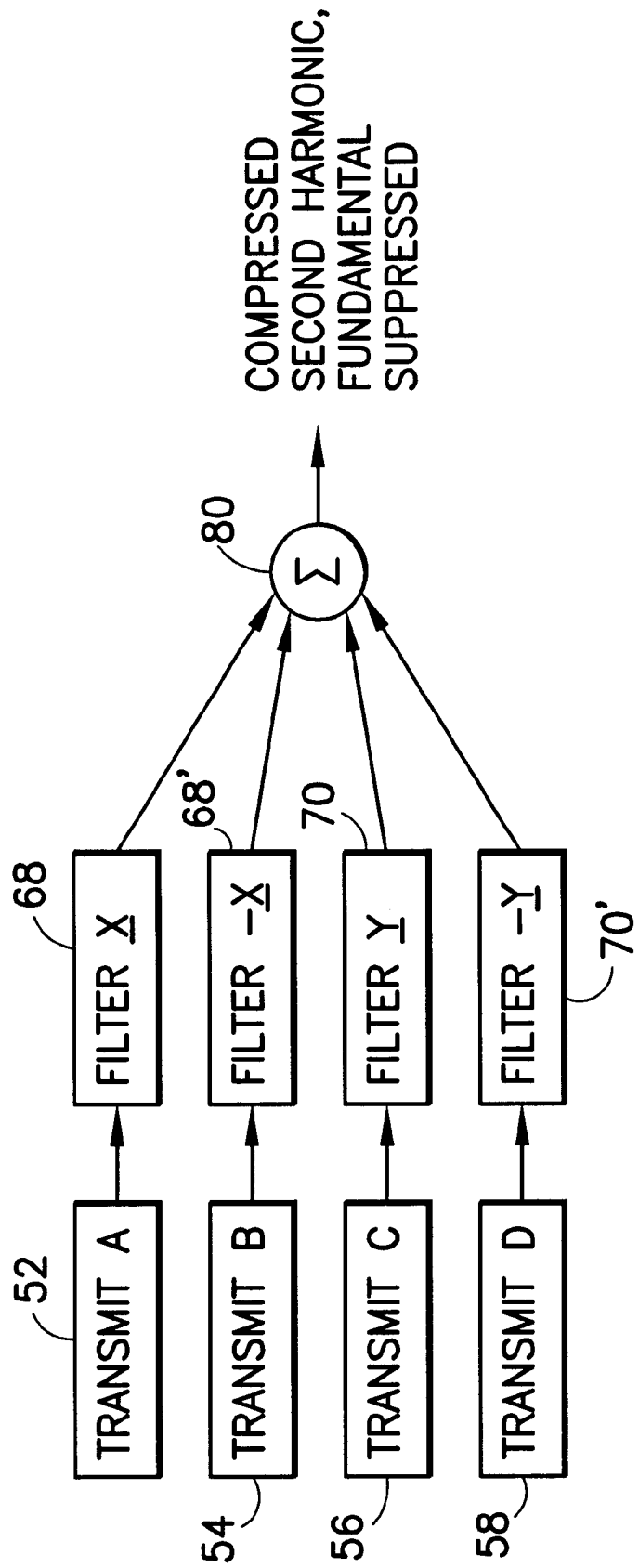
FIG. 8 is a block diagram showing an implementation of a coding and decoding scheme for a Golay code pair (X,Y) in accordance with another preferred embodiment of the invention.

By using the principles of linear systems, all the required signal differences, filters, and sums shown in FIG. 7 may be condensed into the coding and decoding scheme shown in FIG. 8, for efficient implementation. Referring to FIG. 8, received signal 52 from the first transmit A is match filtered with $\underline{X}$ (filter 68), received signal 54 from the second transmit B is match filtered with $-\underline{X}$ (filter 68'), received signal 56 from the third transmit C is match filtered with $\underline{Y}$ (filter 70), and received signal 58 from the fourth transmit D is match filtered with $-\underline{Y}$ (filter 70'). Finally, all four filtered signals are summed in a vector summer 80 to produce the compressed second harmonic signal with suppressed fundamental signal.

The disclosed algorithm may be demonstrated with an example. The notation used in this example is as follows: the subscripts "1" and "2" denote the resulting fundamental and second harmonic signals, respectively, while "u" and "v" denote the second harmonic signal resulting from the "1" and "j" pulses, respectively. The second harmonic signal is related to the square of the fundamental, and it is assumed that a difference exists between the second harmonic signals generated by the "1" and "j" fundamental transmit pulses.

For this example, the Golay pair $X=[1, 1, 1, -1]$ and $Y=[1, 1, -1, 1]$ are used, in wherein $-\underline{X}=[1, -1, -1, -1]$ and $\underline{Y}=[1, -1, 1, 1]$. Using Eqs. (1)–(4), the transmit sequences A through D can be generated as follows: $A=[1, -1, 1, -j]$; $B=[j, -j, j, -1]$; $C=[1, -1, j, -1]$; and $D=[j, -j, 1, -j]$. Using these transmit codes produces the following fundamental and second harmonic signals on reception:

$$A=[1, -1, 1, -j] \to A_1=[1, -1, 1, -j], A_2=[u, u, u, v]$$

$$B=[j, -j, j, -1] \to B_1=[j, -j, j, -1], B_2=[v, v, v, u]$$

$$C=[1, -1, j, -1] \to C_1[1, -1, j, 31\ 1]C_2[u, u, v, u]$$

$$D=[j, -j, 1, j] \to D_1[j, -j, 1, -j], D_2[v, v, u, v]$$

On receive, the second harmonic component is match filtered with $\underline{X}$, $-\underline{X}$, $\underline{Y}$, and $-\underline{Y}$, and then summed to produce a fully compressed second harmonic signal:

$$(A_2-B_2)*\underline{X}+(C_2-D_2)*\underline{Y}=(u-v)[1, 1, 1, -1]*[-1, 1, 1, 1]+(u-v)[1, 1, -1, 1]*[1, -1, 1, 1]=(u-v)[0, 0, 0, 8, 0, 0, 0]$$

with SNR (signal-to-noise ratio) gain=10 log(2L|u-v|), where length L=4 in this example. The same filtering and summation on the fundamental signal produces the null result:

$$(A_1-B_1)*\underline{X}+(C_1-D_1)*\underline{Y}=(1-j)[1, -1, 1, 1]*[-1, 1, 1, 1]+(1-j)[1, -1, -1, -1]*[1, -1, 1, 1]=0$$

The imaging system incorporating the structure shown in FIG. 8 can also operate by demodulating the RF echo signals to baseband and downsampling before or after beamsummation. In this situation, the oversampled sequences would also be demodulated to baseband and downsampled.

The matched filter can be implemented in software or hardware at the beamformer output, as shown in FIG. 2, or at the demodulator output (not shown). In the latter situation, the filter coefficients must be matched to the demodulated signals. For the situation when the demodulator shifts by discrete frequencies $f_d=k/2t_b$, where k is any positive integer and $t_b$ is the duration of the encoded transmit sequence, the sinusoidal becomes real and the same set of filter coefficients is supplied to both matched filters for the I and Q components, which thus form a real filter. In the situations when $f_d \neq k/2t_b$, the I and Q matched filters receive different sets of filter coefficients and thus form a complex filter. In the latter situation, the filter coefficients are matched to the respective demodulated signal component.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A system for transmitting a beam of wave energy, comprising:
   a transducer array comprising a multiplicity of transducer elements;
   a multiplicity of pulsers coupled to respective transducer elements of said transducer array; and
   a transmit beamformer programmed to activate each of said pulsers with a set of transmit focus delays and with respective encoded transmit sequences A, B, C, and D during first through fourth transmit firings, said encoded transmit sequences comprising a base sequence convolved with respective transmit codes, said transmit codes being selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair.

2. The system as recited in claim 1, wherein said transducer elements comprise piezoelectric transducer elements.

3. The system as recited in claim 1, wherein said transmit sequences are encoded using quadrature phase shift keying.

4. The system as recited in claim 1, wherein $X=[1, 1, 1, -1]$ and $Y=[1, 1, -1, 1]$.

5. A method for operating a transducer array to transmit a beam of wave energy, comprising the steps of driving each transducer element of said transducer array forming a transmit aperture with respective encoded transmit sequences A, B, C, and D during first through fourth transmit firings focused at the same focal position, said encoded transmit sequences comprising a base sequence convolved with respective transmit codes, said transmit codes being selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair.

6. The method as recited in claim 5, wherein said transmit sequences are encoded using quadrature phase shift keying.

7. The method as recited in claim 5, wherein $X=[1, 1, 1, -1]$ and $Y=[1, 1, -1, 1]$.

8. An imaging system comprising:
   a transducer array comprising a multiplicity of transducer elements for transmitting wave energy in response to electrical activation and transducing returned wave energy into electrical signals;
   a transmitter coupled to said transducer array and programmed to activate selected transducer elements forming a transmit aperture to transmit focused wave energy encoded with respective encoded transmit sequences A, B, C, and D during first through fourth transmit firings, said encoded transmit sequences comprising a base sequence convolved with respective transmit codes, said transmit codes being selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair;

a receiver programmed to form a respective receive vector from electrical signals supplied from selected transducer elements forming a receive aperture subsequent to each transmit firing;

a matched filter programmed to filter said respective receive vectors as a function of said Golay pair;

a vector summer for summing said filtered receive vectors acquired from said first through fourth transmit firings; and a subsystem for displaying an image having an image portion which is a function of said summed filtered receive vectors.

9. The system as recited in claim 8, wherein said matched filter is programmed with sets of filter coefficients for match filtering said respective receive vectors, said filter coefficient sets comprising $\underline{X}$, $-\underline{X}$, $\underline{Y}$, and $-\underline{Y}$.

10. The system as recited in claim 8, wherein said transmit sequences are encoded using quadrature phase shift keying.

11. The system as recited in claim 8, wherein X=[1, 1, 1, –1] and Y=[1, 1, –1, 1].

12. The system as recited in claim 8, wherein said matched filter comprises a file impulse response filter.

13. The system as recited in claim 8, wherein said subsystem comprises:

a processing subsystem programmed to form an image signal from said summed filtered receive vectors; and a display subsystem programmed to display an image having an image portion which is a function of said image signal.

14. The system as recited in claim 8, wherein said transducer elements comprise piezoelectric elements for transmitting ultrasound waves in response to electrical activation and transducing returned ultrasound waves into electrical signals.

15. An imaging system comprising:

a transducer array comprising a multiplicity of transducer elements for transmitting wave energy in response to electrical activation and transducing returned wave energy into electrical signals;

a transmitter coupled to said transducer array and programmed to activate selected transducer elements forming a transmit aperture to transmit focused wave energy encoded with respective encoded transmit sequences A, B, C, and D during first through fourth transmit firings, said encoded transmit sequences comprising a base sequence convolved with respective transmit codes, said transmit codes being selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair;

a receiver programmed to form a respective receive vector from electrical signals supplied from selected transducer elements forming a receive aperture subsequent to each transmit firing;

means for decoding a harmonic signal component and suppressing a fundamental signal component of said receive vectors; and a subsystem for displaying an image having an image portion which is a function of said decoded harmonic signal component of said receive vector.

16. The system as recited in claim 15, wherein said decoding means comprise:

a matched filter programmed to filter said respective receive vectors as a function of said Golay pair; and a vector summer for summing said filtered receive vectors acquired from said first through fourth transmit firings.

17. The system as recited in claim 16, wherein said matched filter is programmed with sets of filter coefficients for match filtering said respective receive vectors, said filter coefficient sets comprising $\underline{X}$, $-\underline{X}$, $\underline{Y}$, and $-\underline{Y}$.

18. The system as recited in claim 15, wherein X=[1, 1, 1, –1] and Y=[1, 1, –1, 1].

19. The system as recited in claim 15, wherein said decoding means comprise:

a vector subtracter for forming a first difference of the receive vectors acquired from said first and second transmit firings and a second difference of the receive vectors acquired from said third and fourth transmit firings;

a matched filter programmed to filter said first and second differences as a function of said Golay pair; and a vector summer for summing the filtered first and second differences.

20. The system as recited in claim 16, wherein said matched filter is programmed with sets of filter coefficients for match filtering said first and second differences, said filter coefficient sets comprising $\underline{X}$ and $\underline{Y}$.

21. An imaging system comprising:

a transducer array comprising a multiplicity of transducer elements for transmitting wave energy in response to electrical activation and transducing returned wave energy into electrical signals;

a display monitor for displaying an image having an image portion which is a function of an image signal; and a computer programmed to perform the following steps:

(a) activating a plurality of said transducer elements to transmit focused wave energy encoded with respective encoded transmit sequences A, B, C, and D during first through fourth transmit firings, said encoded transmit sequences comprising a base sequence convolved with respective transmit codes, said transmit codes being selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair;

(b) forming a receive vector from electrical signals supplied from selected transducer elements forming a receive aperture subsequent to each transmit firing;

(c) decoding a harmonic signal component and suppressing a fundamental signal component of said receive vectors;

(d) forming an image signal from said decoded harmonic signal component of said receive vectors; and (e) sending said image signal to said display monitor.

22. The system as recited in claim 21, wherein the decoding step comprises the steps of:

match filtering said respective receive vectors as a function of said Golay pair; and vector summing said filtered receive vectors acquired from said first through fourth transmit firings.

23. The system as recited in claim 21, wherein the decoding step comprises the steps of:

forming a first difference of the receive vectors acquired from said first and second transmit firings;

forming a second difference of the receive vectors acquired from said third and fourth transmit firings;

match filtering said first and second differences as a function of said Golay pair; and vector summing said filtered first and second differences.

24. A method of operating an imaging system comprising a multiplicity of transducer elements for transmitting wave energy in response to electrical activation and transducing returned wave energy into electrical signals, and a display monitor for displaying an image having an image portion which is a function of an image signal, said method comprising the steps of:

(a) activating a plurality of said transducer elements to transmit focused wave energy encoded with respective encoded transmit sequences A, B, C, and D during first through fourth transmit firings, said encoded transmit sequences comprising a base sequence convolved with respective transmit codes, said transmit codes being selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair;

(b) forming a receive vector from electrical signals supplied from selected transducer elements forming a receive aperture subsequent to each transmit firing;

(c) decoding a harmonic signal component and suppressing a fundamental signal component of said receive vectors;

(d) forming an image signal from said decoded harmonic signal component of said receive vectors; and (e) sending said image signal to said display monitor.

* * * * *